(12) United States Patent
Fischer et al.

(10) Patent No.: US 8,968,194 B2
(45) Date of Patent: Mar. 3, 2015

(54) METHOD AND MEDICAL SYSTEM FOR ASSISTING A MEDICAL MEASURE IMPLEMENTED BY THE MEDICAL SYSTEM

(75) Inventors: Daniel Fischer, Erlangen (DE); Jasmina Ludwig, Erlangen (DE)

(73) Assignee: Siemens Aktiengesellschaft, Munich (SE)

( * ) Notice: Subject to any disclaimer, the term of this patent is extended or adjusted under 35 U.S.C. 154(b) by 1621 days.

(21) Appl. No.: 12/438,567

(22) PCT Filed: Aug. 30, 2007

(86) PCT No.: PCT/EP2007/059076
§ 371 (c)(1),
(2), (4) Date: Feb. 24, 2009

(87) PCT Pub. No.: WO2008/025833
PCT Pub. Date: Mar. 6, 2008

(65) Prior Publication Data
US 2010/0014635 A1    Jan. 21, 2010

(30) Foreign Application Priority Data
Aug. 31, 2006  (DE) .......................... 10 2006 040 942

(51) Int. Cl.
*A61B 5/00* (2006.01)
*A61B 6/00* (2006.01)
*A61M 21/00* (2006.01)

(52) U.S. Cl.
CPC .......... *A61B 6/502* (2013.01); *A61M 2021/005* (2013.01); *A61M 2021/0044* (2013.01)
USPC ........................................................ 600/300

(58) Field of Classification Search
USPC .............. 600/27, 300–301, 409–410; 40/436; 362/297
See application file for complete search history.

(56) References Cited

U.S. PATENT DOCUMENTS

| | | | | |
|---|---|---|---|---|
| 5,266,070 A | * | 11/1993 | Hagiwara et al. | 600/27 |
| 5,355,885 A | | 10/1994 | Tsuda et al. | |
| 5,425,699 A | * | 6/1995 | Speigel | 600/26 |
| 5,432,544 A | * | 7/1995 | Ziarati | 600/410 |
| 5,627,470 A | | 5/1997 | Kuth | |
| 5,864,331 A | * | 1/1999 | Anand et al. | 345/656 |
| 5,917,395 A | * | 6/1999 | Overweg | 335/296 |
| 6,198,285 B1 | * | 3/2001 | Kormos et al. | 324/318 |
| 6,201,394 B1 | * | 3/2001 | Danby et al. | 324/319 |
| 6,254,527 B1 | * | 7/2001 | August | 600/27 |
| 6,335,623 B1 | * | 1/2002 | Damadian et al. | 324/320 |
| 6,503,188 B1 | * | 1/2003 | August | 600/27 |
| 6,527,700 B1 | * | 3/2003 | Manico et al. | 600/26 |
| 6,554,763 B1 | * | 4/2003 | Amano et al. | 600/26 |
| 6,641,522 B2 | * | 11/2003 | August | 600/27 |
| 6,872,179 B2 | * | 3/2005 | Kamiyama et al. | 600/437 |
| 7,021,813 B2 | * | 4/2006 | Lee et al. | 362/609 |
| 7,331,698 B2 | | 2/2008 | Gösswein et al. | |
| 7,431,689 B2 | * | 10/2008 | Booty et al. | 600/27 |
| 7,823,306 B1 | * | 11/2010 | Kersten et al. | 40/436 |
| 2002/0033791 A1 | * | 3/2002 | Arakawa | 345/102 |
| 2002/0115905 A1 | * | 8/2002 | August | 600/27 |

(Continued)

*Primary Examiner* — William Thomson
*Assistant Examiner* — Bobby Soriano
(74) *Attorney, Agent, or Firm* — Schiff Hardin LLP

(57) ABSTRACT

In a method and a medical installation for assisting in a medical measure implemented by a medical device, a lighting element generates light that uniformly illuminates the medical device or its environment, the illumination being designed to reduce stress on the part of a patient undergoing the medical measure.

10 Claims, 1 Drawing Sheet

(56) References Cited

U.S. PATENT DOCUMENTS

| | | |
|---|---|---|
| 2002/0198438 A1* | 12/2002 | Cromer et al. ............... 600/27 |
| 2004/0254501 A1* | 12/2004 | Mault ........................ 600/587 |
| 2005/0004444 A1 | 1/2005 | Boninger et al. |
| 2005/0162736 A1* | 7/2005 | Cromer et al. ............. 359/450 |
| 2005/0283068 A1* | 12/2005 | Zuccolotto et al. ......... 600/410 |
| 2005/0283076 A1* | 12/2005 | Hangiandreou et al. ..... 600/443 |
| 2006/0064037 A1* | 3/2006 | Shalon et al. ............... 600/586 |
| 2006/0079763 A1* | 4/2006 | Jeung et al. ................. 600/428 |
| 2006/0084846 A1* | 4/2006 | Deluz ......................... 600/300 |
| 2006/0152931 A1* | 7/2006 | Holman ...................... 362/297 |
| 2007/0238934 A1* | 10/2007 | Viswanathan .............. 600/300 |
| 2007/0255588 A1* | 11/2007 | Hamilton ....................... 705/2 |
| 2008/0071136 A1* | 3/2008 | Oohashi et al. ................ 600/27 |
| 2009/0223901 A1* | 9/2009 | Juestel et al. ................ 210/748 |

* cited by examiner

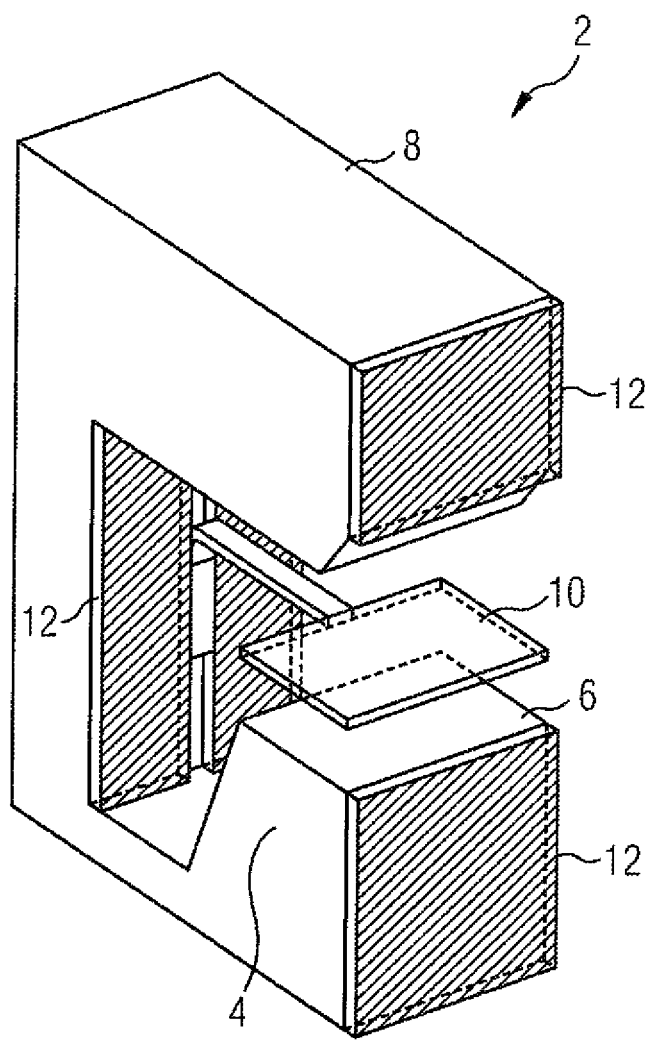

METHOD AND MEDICAL SYSTEM FOR ASSISTING A MEDICAL MEASURE IMPLEMENTED BY THE MEDICAL SYSTEM

BACKGROUND OF THE INVENTION

1. Field of the Invention

The present invention concerns a method to assist a medical measure implemented by a medical system, in particular a mammography system. Moreover, the invention concerns a medical system in which the medical measure is assisted with such a method.

2. Description of the Prior Art

The implementation of a medical measure (patient interaction) implemented with the use of a medical system is in many cases associated with a significant physical and psychological stress on the prior art of the patient. Such stress not only has a negative influence on the well-being of the patient but due to an insufficient willingness of the patient to cooperate, but also may lead to the situation that the medical measure itself (for example the generation of a series of x-ray images of a female breast in mammography) cannot be optimally implemented, i.e. implemented in a short time with the best possible result.

SUMMARY OF THE INVENTION

An object of the present invention is provide a method to support a medical measure implemented with the use of a medical system (in particular with the use of a mammography system) in which the well-being of the patient and therefore the patient's willingness to cooperate are advantageously influenced with little technical expenditure. Moreover, an object of the invention is provide a medical system operating with such a method.

According to the invention, a uniform (ambient) light illuminating the medical system or its surroundings is generated with at least one illumination element or lamp. A comfortable atmosphere for the patient is thereby achieved in the environment of the medical system. This is particularly advantageous in the implementation of a mammogram since the pressure exerted by the compression plate on the breast of the patient leads to an uncomfortable stressing of the patient that can be subjectively alleviated via a comfortable environmental atmosphere.

The medical measure in the sense of the present invention can be both a procedure implemented with the assistance of the medical system (for example a tomography system or a mammography system), for example an image-assisted biopsy. The medical measure can also merely consist of acquiring diagnostically usable information with an imaging medical system, for example in the form of 2D or tomosynthetic 3D x-ray images in mammography.

The at least one illumination element can permanently installed in a room in which the measure is implemented with the medical system. However, a particularly flexible solution is achieved when the at least one illumination element is directly integrated into the medical system.

Such a comfortable ambient illumination is in particular achieved when diffusely scattered light is generated that exits into the environment of the medical system. If the color of the light is additionally varied, the patient's subjective sense of time is moreover positively affected, meaning that the duration of the measure is subjectively perceived to be not as long.

In a particularly advantageous embodiment of the method, the progress of the medical measure is tracked by variation of the color of the illumination, for example varied from a rich, robust color tone at the beginning of the measure to a soft, light color tone at the end of the measure.

With regard to the medical system, the object is achieved according to the invention by a medical system having at least one illumination element to generate a uniform light illuminating the system or its surroundings.

BRIEF DESCRIPTION OF THE DRAWINGS

The single FIGURE shows an exemplary embodiment of the invention in the form of a mammography system, shown in a schematic perspective presentation.

DESCRIPTION OF THE PREFERRED EMBODIMENTS

According to the FIGURE, the medical system 2 (a mammography system in the example) has a support table 4 with a support plate 6 in which an x-ray detector is arranged. An x-ray source is located in an arm 8 above the support table 4. A transparent compression plate 10 with which the breast of a patient on the bearing plate 6 is pressed is mounted in a height-adjustable manner between the arm 8 and the support table 4.

Flat lamps or illumination elements 12 (highlighted by shading in the image) are located at the apparatus 2 in the form of diffusion discs or diffusion plates behind which light sources (not visible) are arranged. The diffusion discs diffusely scatter the light generated by the light sources and escaping into the environment so that the illumination elements 12 uniformly illuminate both the system 2 and its surroundings and generate a comfortable ambient light.

The illumination elements 12 can alternatively or additionally be arranged in the surroundings of the system 2 in order to generate in this way an ambient environmental light in the room itself in which the medical measure is implemented.

Instead of or in addition to measures with which diffuse, scattered light is generated, other creative illumination elements (for example items are known as light-collecting plastic elements) can also be arranged at the apparatus 2 or in the environment of the apparatus 2, into which elements environmental light enters and is conducted to the edges at which it exits with greater intensity, in order to achieve in this manner a comfortable, aesthetically pleasing environmental atmosphere increasing the well-being of the patient, for example.

The invention is explained as an example using a simple mammography system but the invention can be particularly advantageously used in medical systems that are used in the framework of medical measures that are connected with a large time demand, for example in particular in tomosynthesis-capable mammography systems or other imaging systems that enable the reconstruction of 3D images of the inside of the body of a patient.

Although modifications and changes may be suggested by those skilled in the art, it is the intention of the inventors to embody within the patent warranted heron all changes and modifications as reasonably and properly come within the scope of their contribution to the art.

We claim as our invention:

1. A method to assist a medical measure implemented with a medical device, comprising the steps of:
    implementing a medical measure by interacting with a patient using a medical device having a device housing, said housing having a plurality of exterior housing panels that are situated in a field of view of the patient while the patient is interacting with the medical device; and directly attaching at least one flat lamp to each of said plurality of exterior housing panels of said device housing in said field of view and uniformly illuminating each of said plurality of exterior panels of said device housing in said field of view with light exiting from said at least one flat lamp.

2. A method as claimed in claim 1 comprising implementing a mammographic examination of the patient as said medical measure, using a mammography system as said medical device.

3. A method as claimed in claim 1 comprising diffusely scattering light exiting from said flat lamp.

4. A method as claimed in claim 1 comprising automatically varying a color of said light.

5. A method as claimed in claim 4 comprising varying the color of said light in a variation pattern that tracks progress of the implementation of said medical measure with said medical device.

6. A medical system comprising:
- a medical device configured to interact with a patient to implement a medical measure, said medical device having a device housing, said housing having a plurality of exterior housing panels that are situated in a field of view of the patient while the patient is interacting with the medical device; and
- at least one flat lamp directly attached to each of said plurality of exterior housing panels of said device housing in said field of view, each flat lamp emitting light that uniformly illuminates the respective panel to which that flat lamp is directly attached.

7. A medical system as claimed in claim 6 wherein said medical device is a mammography device.

8. A medical system as claimed in claim 6 comprising a light diffuser that diffuses light emitted by said flat lamp to generate a diffusely scattered light pattern at said medical device.

9. A medical system as claimed in claim 6 comprising a control unit that automatically varies a color of the light.

10. A medical system as claimed in claim 9 wherein said control unit is configured to vary the color of said light in a variation pattern that tracks progress of the implementation of said medical measure.

* * * * *